(12) United States Patent  
Nutting (10) Patent No.: US 8,517,734 B1  
(45) Date of Patent: Aug. 27, 2013

(54) COMFORTABLE REMOVABLE TOOTH CAP

(75) Inventor: Donald W. Nutting, Boulder, CO (US)

(73) Assignee: Foothills Creations Ltd, Boulder, CO (US)

( * ) Notice: Subject to any disclaimer, the term of this patent is extended or adjusted under 35 U.S.C. 154(b) by 1735 days.

(21) Appl. No.: 11/677,014

(22) Filed: Feb. 20, 2007

Related U.S. Application Data

(63) Continuation-in-part of application No. 11/366,902, filed on Mar. 1, 2006.

(51) Int. Cl.  
*A61C 13/225* (2006.01)

(52) U.S. Cl.  
USPC ........................................................ 433/183

(58) Field of Classification Search  
USPC ........... 433/180–183, 218–221, 229; 472/70, 472/133  
See application file for complete search history.

(56) References Cited

U.S. PATENT DOCUMENTS

| | | | |
|---|---|---|---|
| 758,750 A * | 5/1904 | Haldeman | 433/221 |
| 996,921 A * | 7/1911 | Goslee | 433/218 |
| 1,379,063 A | 5/1921 | Van Allen | |
| 2,057,341 A | 10/1936 | Morgan | |
| 3,558,540 A | 1/1971 | Molnar | |
| 3,793,728 A | 2/1974 | Corbineau | |
| 4,015,332 A | 4/1977 | Manne | |
| 4,206,545 A | 6/1980 | Lard | |
| 4,251,215 A | 2/1981 | May et al. | |
| 4,430,061 A | 2/1984 | Webb et al. | |
| 4,678,435 A | 7/1987 | Long | |
| 4,738,622 A | 4/1988 | Kawahara et al. | |
| 5,102,337 A | 4/1992 | Soroca | |
| 5,324,198 A | 6/1994 | Hazen | |
| 5,403,186 A | 4/1995 | Ginsburg | |
| 5,547,381 A | 8/1996 | Nutting | |
| 5,569,036 A | 10/1996 | Goldiner et al. | |
| 5,951,294 A * | 9/1999 | Pierson | 433/218 |

FOREIGN PATENT DOCUMENTS

WO 9103210 3/1991

OTHER PUBLICATIONS

Generik Ink, Inc. Why Not Party? Horror Film Make-Up instruction sheet, 1988.  
Fangtastics fang instruction sheet.  
Scarecrow Custom Fangs instruction sheet.  
262 Cheap Scarecrow Fang photographs.  
373 Original Fangtastics Fang photographs.  
449 New Fangtastics Fang photographs.  
386 Professional Fangtastics Fang photographs.  
419 New Bloody Mary Fang photographs.  
224 Norben Fang photographs.  
421 Hot Topic Fang photographs.

(Continued)

*Primary Examiner* — Cris L Rodriguez  
*Assistant Examiner* — Hao D Mai  
(74) *Attorney, Agent, or Firm* — Brian D. Smith, PC (57) ABSTRACT

A removable tooth cap defines a cavity for receiving a real tooth as well as material for removably attaching the tooth cap to the real tooth. The tooth cap has a front side and a back side which form a tip at the distal or free end of the tooth cap. The back side has a length which is less than ⅔ of the overall length of said tooth cap. The back side further defines a hole for receiving the material so that said material anchors or locks to the tooth cap when the material hardens.

18 Claims, 8 Drawing Sheets

(56) References Cited

OTHER PUBLICATIONS

433 Fun World Fang photographs.
324 Old Foothills design Fang photographs.
Fun World Tooth Cap Drawing.
Fangtastics fang instruction sheet (date unknown—admitted prior art).
Scarecrow Custom Fangs instruction sheet (date unknown—admitted prior art).
262 Cheap Scarecrow Fang photographs (date unknown—admitted prior art).
373 Original Fangtastics Fang photographs (date unknown—admitted prior art).
449 New Fangtastics Fang photographs (date unknown—admitted prior art).
386 Professional Fangtastics Fang photographs (date unknown—admitted prior art).
410 New Bloody Mary Fang photographs (date unknown—admitted prior art).
224 Norben Fang photographs (date unknown—admitted prior art).
421 Hot Topic Fang photographs (date unknown—admitted prior art).
433 Fun World Fang photographs (date unknown—admitted prior art).
324 Old Foothills design Fang photographs (date unknown—admitted prior art).
Fun World Tooth Cap drawing drawn by inventor Donald Nutting (date unknown—admitted prior art).

* cited by examiner

COMFORTABLE REMOVABLE TOOTH CAP

CROSS REFERENCE TO RELATED APPLICATION

This application is a continuation-in-part of U.S. patent application Ser. No. 11/366,902 filed on Mar. 1, 2006.

FIELD OF THE INVENTION

The invention relates generally to removable tooth caps and more particularly to removable tooth caps providing a realistic appearance and a comfortable fit.

BACKGROUND OF THE INVENTION

In the course of parties, particularly Halloween parties, it is common to have people masquerade as vampires and other wild beasts. In doing so, these people are faced the problem of using tooth caps that simulate fangs.

The first company to produce preformed universal tooth cap bodies was Violet's with their Fangtastics brand of fangs. Scarecrow followed with their individual tooth caps commonly known as Scarecrow Fangs. Thirdly, Foothills LTD followed with their Custom Dracula Fangs. Other fangs that followed appear to imitate in one form or another one of these three tooth cap bodies. Fun World came out with a tooth cap that imitated the Scarecrow tooth cap, but with a hole in the back of the tooth cap.

The Fangtastics design of a tooth cap body, with its shallow cavity trough for tooth insertion, was unstable, and the fangs had a tendency to fall out. The Scarecrow Fangs design has a deep cavity trough which attempts to provide adequate tooth support, but lacks a comfortable fit with a good bite. Foothills LTD's Custom Dracula Fangs design also has a deep cavity trough providing good tooth support, and a comfortable fit with a good bite. However, when making a partial plate with the fang before the attaching material hardens, the wearer sometimes pushes the fang forward when biting down to achieve a natural bite. This pushing forward of the fang causes the appearance of the fang to not be as realistic as it could be. The Fun World tooth cap, which as mentioned is a Scarecrow imitation, added a hole in the back side of the tooth cap to improve anchoring of the attaching material to the tooth cap, but with no other purpose in mind. A significant problem with the Fun World tooth cap is that its back side is almost as long as its front side and therefore often interferes with the wearer's opposing teeth when the wearer bites down, i.e. brings the upper and lower jaws together in their normal occlusion.

SUMMARY OF THE INVENTION

A major object of the present invention is to provide a custom fit tooth cap that has a more comfortable fit and a better bite for the wearer, while not interfering with the placement or mounting of the tooth cap on the wearer's real tooth so as to not detract from the realistic appearance provided by the tooth cap or interfere with the user's normal occlusion when the tooth cap is attached to the user's real tooth.

Another object of the present invention is to enhance attachment of the material used to attach the tooth cap to the real tooth to the tooth cap.

Yet another general object of the present invention is to provide an inexpensive tooth cap that attaches to a real tooth without any need for specialized equipment or specialized training.

Additional objects, advantages, and novel features of the present invention shall be set forth in part in the description that follows, and in part will become apparent to these skilled in the art upon examination or may be learned by the practice of the invention. The objects and the advantages may be realized and attained by means of the instrumentalities and in combinations particularly pointed out in the appended claims.

To achieve the forgoing and other objects and in accordance with the purposes of the present invention, as embodied and broadly described herein, the present invention provides a removable tooth cap which defines a cavity for receiving a real tooth as well as material for removably attaching the tooth cap to the real tooth. The tooth cap has a front side and a back side with the back side being shaped so as to minimize contact with opposing teeth when the teeth of the upper and lower jaws are brought together in their normal occlusion.

In a preferred embodiment of the present invention, the back side of the tooth cap has a length which is less than ⅔ of the overall length of said tooth cap. In a more preferred embodiment, the back side of the tooth cap has a length which is about ⅓ of the overall length of said tooth cap. The back side further defines a hole for receiving the material for removably attaching the tooth cap to the real tooth so that the material anchors or locks to said tooth cap when the material hardens.

Another preferred embodiment of the present invention provides a removable tooth cap defining a cavity for receiving a real tooth as well as material for removably attaching said tooth cap to the real tooth. This tooth cap has a front side and a back side wherein the cavity includes a generally concave surface defined by an inside surface of the front side. The inside surface of the front side terminates at a peripheral edge which adjoins the front surface of the front side. The back side of this embodiment also preferably has a length which is less than ⅔ of the overall length of said tooth cap and the back side is also generally parallel to the aforesaid peripheral edge. The back side further defines a hole for receiving the attaching material so that said material anchors or locks to the tooth cap when said material hardens.

Yet another preferred embodiment of the present invention provides a removable tooth cap defining a cavity for receiving a real tooth as well as material for removably attaching said tooth cap to the real tooth. This tooth cap has a front side and a relatively short or abbreviated back side wherein the cavity includes a generally concave surface defined by an inside surface of said front side and wherein the inside surface of said front side terminates at a peripheral edge which adjoins the front surface of said front side. The front side and back side also define a lower extension section which forms a tip at the distal end of the tooth cap so that the tooth cap will look like a fang when attached to a person's real tooth. The lower extension section of the tooth cap further defines a ledge surface which connects the back side to the concave surface of said cavity and the lower extension section also defines a hole in the ledge surface for receiving the attaching material so that the material anchors or locks to said tooth cap when it hardens.

As indicated, in this embodiment the back side is preferably short or abbreviated (less than ⅓ the tooth cap's overall length). Ideally and as shown in FIGS. 19-28, the backside's height is about 25% of the tooth cap's overall height or length. In addition, the back side is generally parallel to the peripheral edge of the tooth cap. This short back side and generally parallel orientation of the back side to the peripheral edge is provided so as to eliminate or strongly minimize contact with opposing teeth when the teeth of the upper and lower jaws are brought together in their normal occlusion. The support, instead of being provided by the long or high back of the tooth cap as in Fun World's tooth cap, is instead provided by the surrounding attaching material which flows into the hole and hardens. Since the attaching material is formable or flowable before it hardens, when the wearer bites down on the tooth cap during the process of making a partial plate with the tooth cap, the attaching material will automatically conform to the wearer's teeth including the opposing teeth so that the partial plate thus formed (which includes the tooth cap and hardened attaching material) will not interfere with the opposing teeth when the teeth of the upper and lower jaws are brought together in their normal occlusion.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

In the Drawings.

DETAILED DESCRIPTION OF THE PREFERRED EMBODIMENTS

Figure 7:
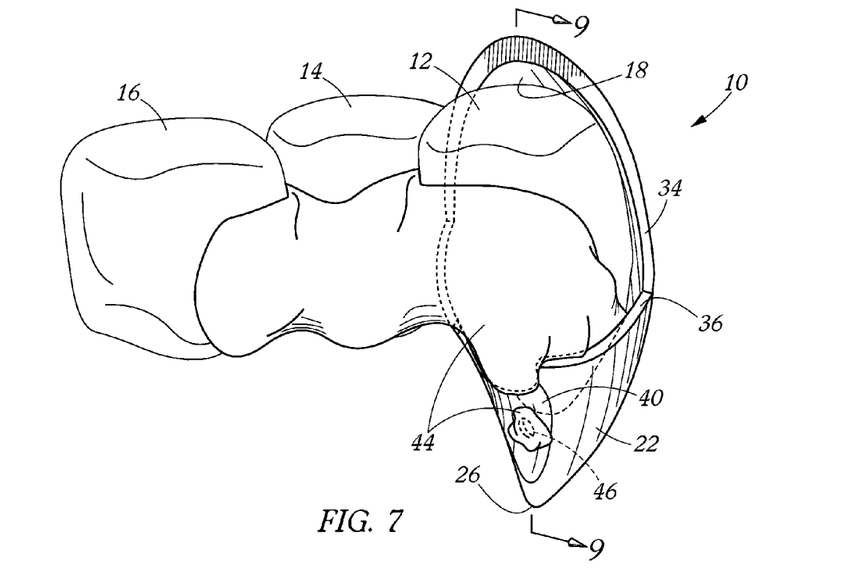
FIG. 7 is a perspective view showing the tooth cap of FIG. 1 mounted on the left upper canine tooth and anchored to the first and second upper left premolars looking from the inside of a wearer's mouth to the outside. The tooth cap is positioned on the canine tooth and a portion of thermoplastic material extends from the cavity inside the tooth cap to the first and second premolars.

Turning now to the drawings, FIGS. 1 through 6 illustrate a tooth cap 10 in isolation. FIG. 7 shows tooth cap 10 mounted or positioned on an individual's left upper canine tooth 12. While shown on a canine tooth, the tooth cap could be mounted on any other canine tooth, an incisor tooth, or any other tooth capable of being received in the cavity 18 of the tooth cap. As also shown, tooth cap 10 includes a generally convex shaped front side 20 and back side 22 which converge together to form an extension 24, a tip 26, and a trough 28 of the tooth cap's cavity 18. As perhaps best shown in FIG. 8, cavity 18 is defined by generally concave shaped inside surfaces 30, 32 of the tooth cap's front and back sides 20, 22, respectively. As also shown, the concave shaped inside surface 30 of front side 20 terminates at a generally flat peripheral edge or rim 34 which adjoins the front surface (not numbered) of said front side. In addition, the inside surface 32 of the back side 22 terminates at an edge 36 referred to as back edge 36 which abuts rim 34. As further shown, back edge 36 is generally flat except along its central section which is referred to herein as the central arcuate cutout edge 38.

Figure 3:
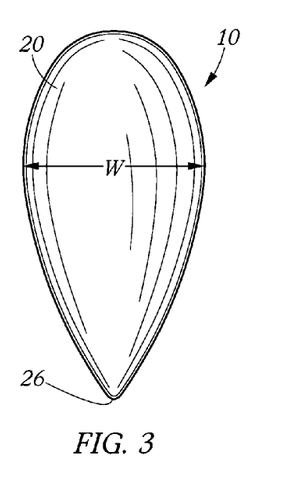
FIG. 3 is a front elevational view of the tooth cap of FIG. 1.
Figure 4:
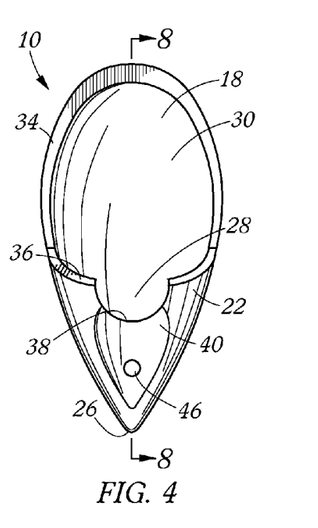
FIG. 4 is a rear elevational view of the tooth cap of FIG. 1.
Figure 5:
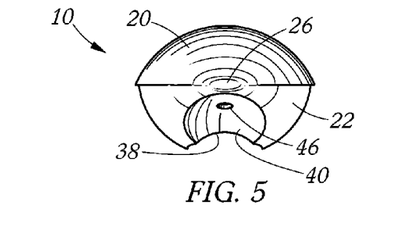
FIG. 5 is a bottom plan view of the tooth cap of FIG. 1.
Figure 6:
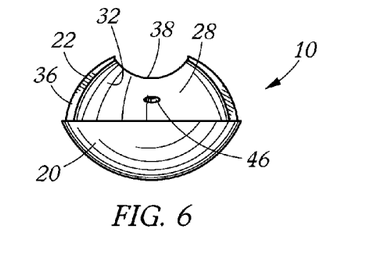
FIG. 6 is a top plan view of the tooth cap of FIG. 1.

As shown in FIG. 3, tooth cap 10 is provided with an appropriate width W, size, and shape to conform to the lateral side of real tooth 12 so that when the tooth cap is placed on the real tooth, the tooth cap becomes a realistic and natural appearing extension of the real tooth. The outside surface (not numbered) of front side 20 has a convex shape to further accentuate the realistic visual effect of the tooth cap for the masquerader, as well as provide sufficient thickness to accommodate the cavity 18 extending therein from the inside, as described above and shown in FIGS. 4 and 8.

Figure 8:
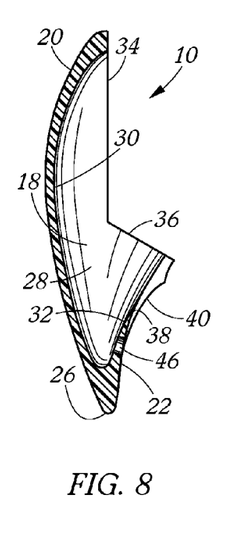
FIG. 8 is a cross sectional view taken along lines 8-8 of FIG. 4.

When tooth cap 10 is worn by the masquerader (also referred to as the wearer or user herein) the extremity edge of the real tooth is preferably positioned in the cavity trough 28 as shown in FIGS. 7, 8 which restricts or eliminates lateral motion of the tooth cap relative to the real tooth, especially when material for attaching the tooth cap to the real tooth is introduced into the cavity trough as described in more detail below.

Figure 9:
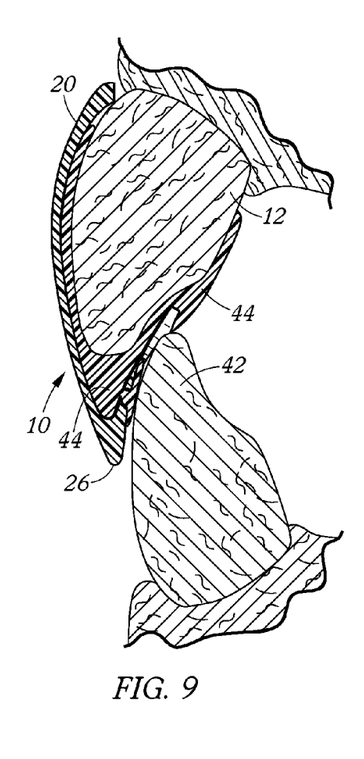
FIG. 9 is a cross sectional view similar to FIG. 8 which additionally shows the tooth cap of FIG. 1 mounted on and attached to a user's real tooth as well as an opposing tooth of the user received in the recessed area of the tooth cap.

In addition, as shown in FIGS. 4-6 and 8, the tooth cap's generally convex shaped back side 22 defines a concave shaped recessed area 40 which extends longitudinally along the back side of the tooth cap from an area adjacent the tip 26 (free distal end) of the tooth cap. As also shown, the back side 22 and recessed area 40 terminate at back edge 36 and central cutout edge 38, respectively, near the mid-section of the tooth cap so that the recessed area 40 opens into cavity 18 (more specifically cavity trough 28) of the tooth cap. As such, an opposing tooth 42 of the wearer can ride or be received in the recessed area 40 and the cavity of the tooth cap when the wearer bites down with the tooth cap, as shown in FIG. 9.

In addition, by providing this recessed area 40 or path for the wearer's opposing tooth, pushing forward of the tooth cap on the wearer's real tooth is prevented or at least minimized, thereby insuring a realistic appearance of the tooth cap when fit on the wearer's real tooth. Moreover, all of this is accomplished without significantly interfering with the wearer's normal occlusion.

Figure 1:
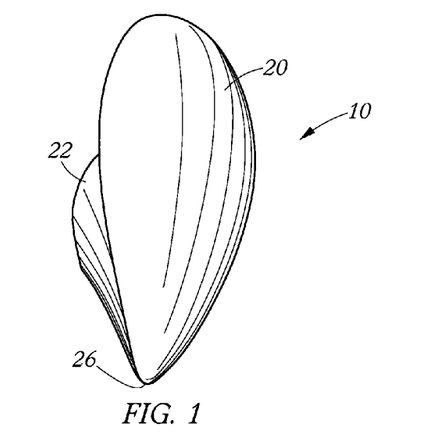
FIG. 1 is a perspective view of a tooth cap of the present invention.
Figure 2:
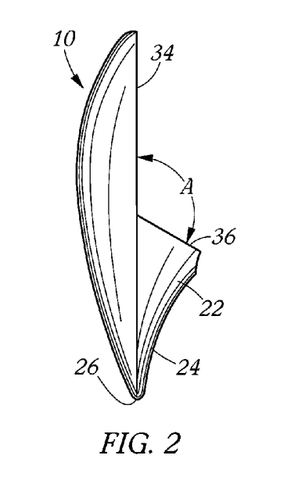
FIG. 2 is a side elevational view of the tooth cap of FIG. 1 which shows the angle A or slope of the back edge of the tooth cap's back side.

To further insure that the tooth cap does not interfere with the wearer's normal occlusion and yet provide sufficient side support from back side 22, back edge 36 is cut back (relative to the corresponding back edge of the tooth cap shown in my previously issued U.S. Pat. No. 5,547,381 which is incorporated herein by reference) so that back edge 36 forms an included angle A of about 120 degrees with peripheral rim 34, as shown in FIG. 2. While a 120 degree included angle is shown, good results should be obtainable with an included angle greater than about 100 degrees with preferred results expected between 100 and 130 degrees.

A preferred method for attaching tooth cap 10 to a real tooth is described in my U.S. Pat. No. 5,547,381. As generally described therein, a quantity of thermoplastic material (shown herein in FIG. 9 as thermoplastic 44) is placed in cavity 18 and cavity trough 28 after it has been heated and is thereby in a flowable state. The tooth cap with flowable thermoplastic material contained therein is then placed on the real tooth and the excess thermoplastic is spread by the user over the adjacent teeth 14, 16 (or other adjacent teeth, not shown) to make a partial plate for the wearer which comprises the tooth cap and the thermoplastic and which securely attaches the tooth cap to the user's teeth when the thermoplastic hardens but which also enables the tooth cap to be easily removed from the user's teeth due to the resiliency of the hardened thermoplastic which allows the partial plate to be easily removed from the teeth even though the thermoplastic has hardened. As also shown in FIG. 7, attachment of the thermoplastic material to the tooth cap 10 is enhanced by providing the tooth cap with a hole 46 which allows the flowable thermoplastic to flow through the hole and onto the surface of recessed area 40. When the thermoplastic material hardens as also described in my U.S. Pat. No. 5,547,381, the tooth cap will be securely attached to the hardened thermoplastic. As also shown in FIG. 7, thermoplastic material also flows over cutout edge 38 onto the recessed area which further enhances attachment of the thermoplastic to the tooth cap when it hardens.

Figure 10:
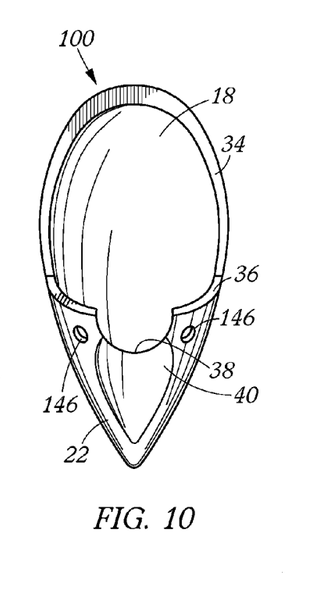
FIG. 10 is a rear elevational view of a tooth cap which is identical to that of FIG. 1 except that the tooth cap of FIG. 10 is provided with a pair of holes 146 instead of the single hole 46 provided in the tooth cap of FIG. 1.

FIG. 10 shows another tooth cap 100 which is identical to tooth cap 10 except that tooth cap 100 is provided with a pair of holes 146 instead of a single hole 46. The use of two holes instead of one is expected to provide better attachment or anchoring of the attaching material to the tooth cap.

Figure 11:
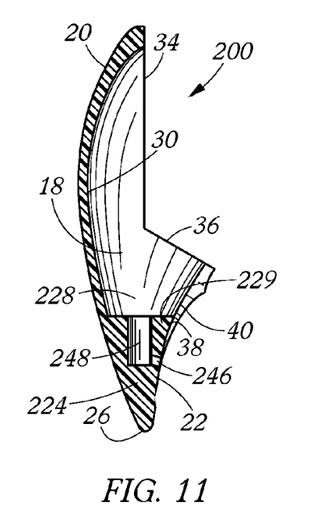
FIG. 11 is a cross sectional view of another tooth cap which is similar to the view of FIG. 8.
Figure 12:
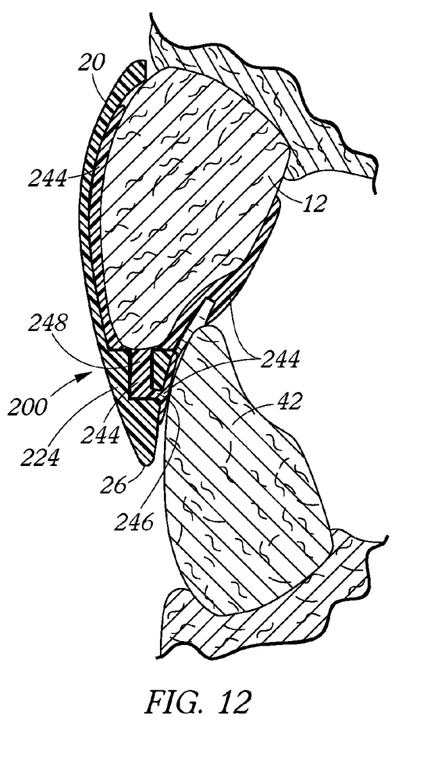
FIG. 12 is another cross sectional view of the tooth cap of FIG. 11 which is similar to the view of FIG. 9.
Figure 13:
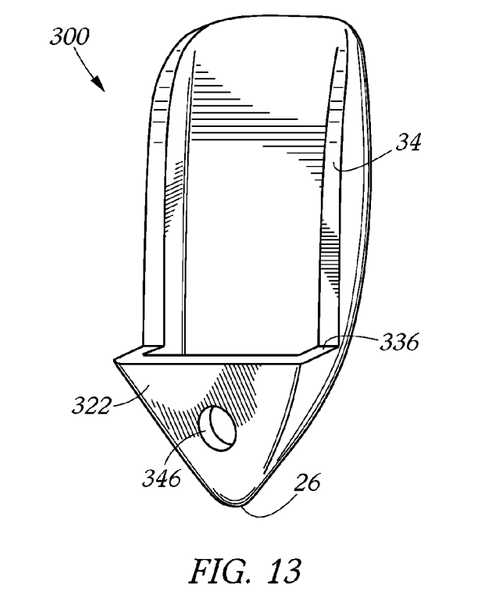
FIG. 13 is a perspective view of another tooth cap of the present invention.

FIGS. 11 and 12 illustrate yet another tooth cap 200 which is similar to tooth cap 10 and utilizes the same reference numerals to identify features which are the same in both embodiments. While similar, it will be appreciated that the cavity trough 228 of tooth cap 200 is shallower than trough 28 of tooth cap 10. As such, the bottom surface 229 of trough 228 is raised relative to that of tooth cap 10. In addition, it will be appreciated that extension 224 of tooth cap 200 is provided with a cylindrically shaped passageway 248 which extends through and from bottom surface 229 to another cylindrically shaped passageway 246 which extends through the outer surface (not numbered) of the tooth cap's backside 22. As shown, passageways 246 and 248 are in fluid communication with each other and thereby allow flowable thermoplastic 244 which is placed in cavity trough 228 to flow through passageways 248, 246 to the outside surface of the tooth cap's extension, as shown in FIG. 12. When the thermoplastic cools and hardens as shown in FIG. 12 about the wearer's tooth 12, in the bottom of the trough 228, in passageways 246, 248 and on the outer surface of the backside of the tooth cap, an extremely strong mechanical bond (anchoring) between the thermoplastic and the tooth cap 200 is provided, thereby insuring that the thermoplastic will remain securely attached to the tooth cap and as such enable the user to reuse the tooth cap for years if desired. While this embodiment shows two passageways adjoining each other at an angle so as to make a bend, any nonlinear passageway capable of receiving flowable thermoplastic or a similar material should form an extremely strong mechanical bond between the material and the tooth cap, essentially locking the material to the tooth cap when the material hardens. In fact, it is not even necessary that the passageway extend through the outer surface of the tooth cap. However, by extending the passageway through the tooth cap's outer surface preferably the back side surface, air pocket formations in the passageway are less likely to occur. Air pockets in the passageway are undesirable because they can prevent the material from flowing into the passageway and forming a strong bond between the material and the tooth cap.

Figure 14:
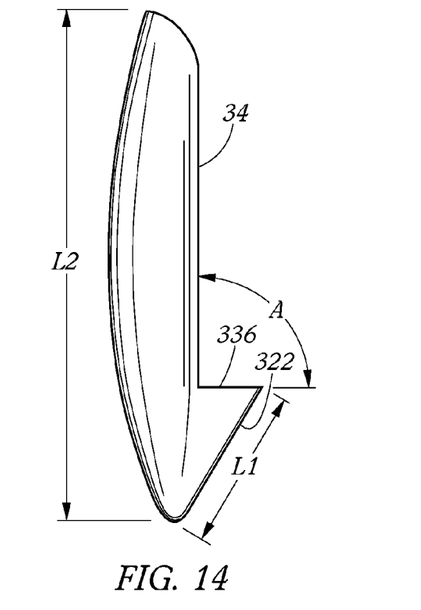
FIG. 14 is a side elevational view of the tooth cap of FIG. 13.
Figure 15:
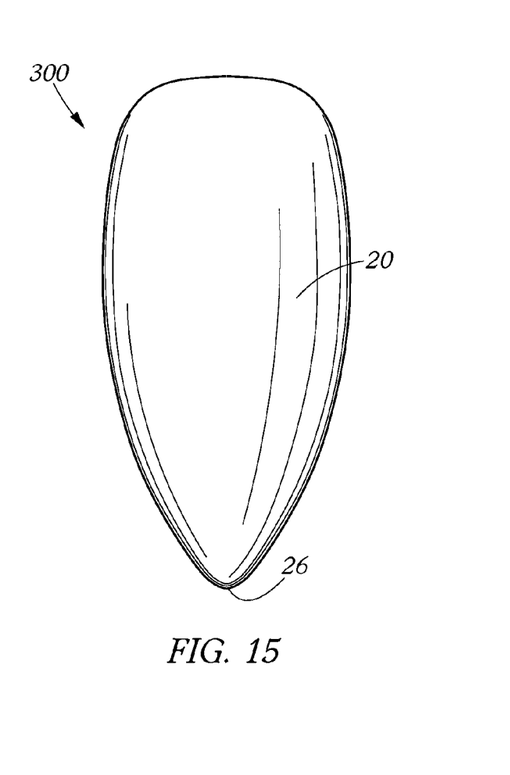
FIG. 15 is a front elevational view of the tooth cap of FIG. 13.
Figure 16:
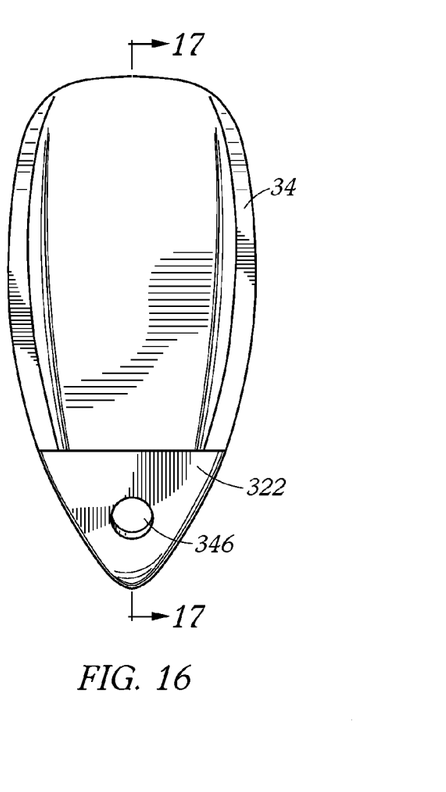
FIG. 16 is a rear elevational view of the tooth cap of FIG. 13.
Figure 17:
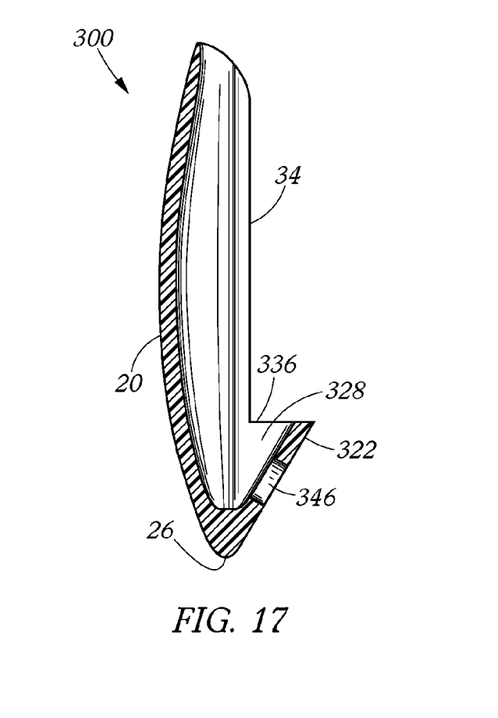
FIG. 17 is a cross sectional view taken along lines 17-17 of FIG. 16.

FIGS. 13 through 18 illustrate a tooth cap 300 which is similar to tooth cap 10 and utilizes the same reference numerals to identify features which are the same in both embodiments. While similar, it will be appreciated that the back edge 336 of tooth cap 300 is cut back so that it forms an included angle A of about 90 degrees with peripheral rim 34, as shown in FIG. 14. While a 90 degree angle is less than the preferred angle of 100 degrees or more of the first embodiment shown herein, it has been found that a right angle as shown will work (indeed angles even less than 90 degrees will work) and not interfere with the wearer's normal occlusion as long as the overall length of the tooth cap's back side 322 has a length L1 as shown in FIG. 14 which is less than ⅔ the overall length L2 of the tooth cap, as also shown in FIG. 14. While L1 should be less than ⅔ the overall length L2, better results should be obtainable if L1 is less than ½ the overall length L2. Even better results should be obtainable if L1 is less than ⅓ the overall length L2 which is roughly what is shown in FIG. 14. Good results may also be obtainable where L1 is only ⅕ or ¼ of L2.

Figure 18:
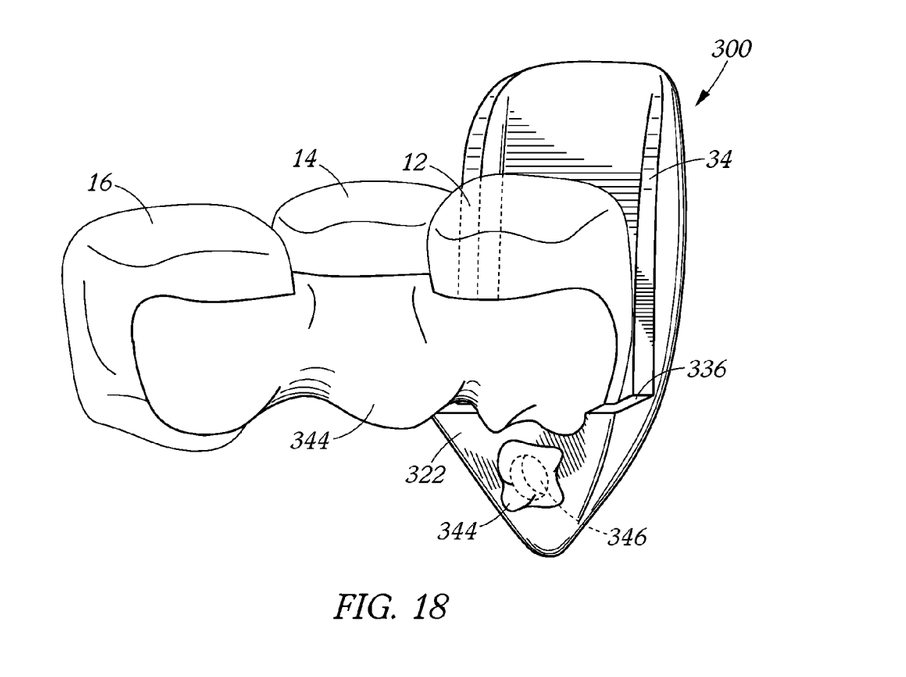
FIG. 18 is a perspective view similar to FIG. 7 showing the tooth cap of FIG. 13 mounted on the left upper canine tooth and anchored to the first and second upper left premolars looking from the inside of a wearer's mouth to the outside. The tooth cap is positioned on the canine tooth and a portion of thermoplastic material extends from the cavity inside the tooth cap to the first and second premolars.
Figure 19:
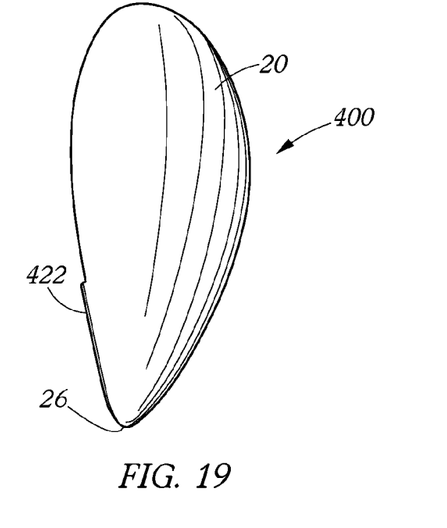
FIG. 19 is a perspective view of another tooth cap of the present invention.
Figure 20:
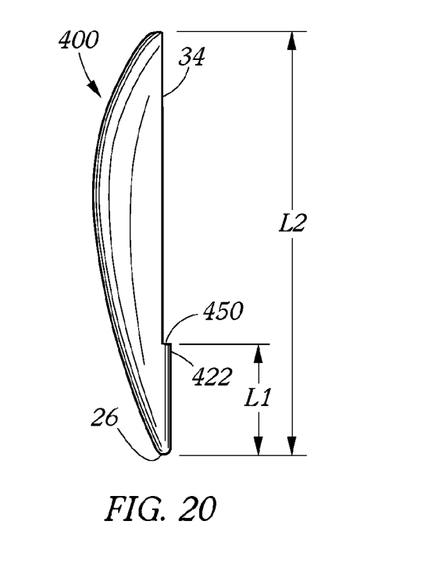
FIG. 20 is a side elevational view of the tooth cap of FIG. 19.
Figure 21:
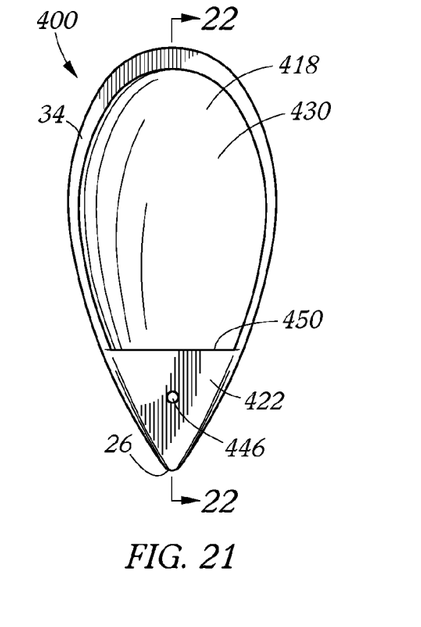
FIG. 21 is a rear elevational view of the tooth cap of FIG. 19.

Tooth cap 300 is also provided with a larger diameter hole 346 which functions similarly to hole 46 in that it allows flowable thermoplastic 344 or any suitable flowable but hardenable material which is placed in cavity trough 328 to flow through hole 346 onto the back side 322 of the tooth cap, as shown in FIG. 18. As discussed in the earlier embodiments, when the thermoplastic cools and hardens as shown in FIG. 18 about the wearer's tooth 12, in the bottom of the trough 328, in hole 346 and on back side 322 of the tooth cap, an extremely strong mechanical bond (anchoring) between the thermoplastic and the tooth cap 300 is provided, thereby insuring that the thermoplastic or other flowable but hardenable attaching material will remain securely attached to the tooth cap and as such enable the user to reuse the tooth cap for years if desired.

FIGS. 19 through 25 illustrate a tooth cap 400 which is also somewhat similar to tooth cap 10 and utilizes the same reference numerals to identify features which are the same in both embodiments. Front side 20 and back side 422 define a lower extension section 424 which forms a tip 26 at the distal end of the tooth cap so that the tooth cap will look like a fang when attached to a person's real tooth. In addition, extension 424 defines a ledge surface 450 which connects back side 422 to the concave surface 430 of the tooth cap's cavity 418. As shown, ledge surface adjoins concave surface 430 of said cavity at an angle of about 90 degrees while adjoining back side 422 at an angle of about 270 degrees.

It will also be appreciated that in this embodiment back side 422 is relatively short or abbreviated (about 25% of the tooth cap's overall height or length) as well as generally flat and parallel to the tooth cap's peripheral edge 34. This embodiment has been found to be particularly suitable for individuals having no overbite. This short back side and general parallel orientation of the back side to the peripheral edge is provided so as to eliminate or strongly minimize contact with opposing teeth when the teeth of the upper and lower jaws are brought together in their normal occlusion. Fang support which conventionally is provided by a longer back side (such the long or high back of the tooth cap as in Fun World's tooth cap), is instead in this embodiment provided by the surrounding attaching material which flows into the passageways 446, 448 and hardens. Since the attaching material is formable or flowable before it hardens, when the wearer bites down on the tooth cap during the process of making a partial plate with the tooth cap, the attaching material will automatically conform to the wearer's teeth including the opposing teeth so that the partial plate thus formed (which includes the tooth cap and hardened attaching material) will not interfere with the opposing teeth when the teeth of the upper and lower jaws are brought together in their normal occlusion. As those skilled in the art will appreciate, this embodiment is particularly suitable for individuals with no overbite who have trouble using conventional fangs with high backsides since the high back sides of these fangs often interfere with their opposing teeth when the teeth of the upper and lower jaws are brought together in their normal occlusion.

Figure 22:
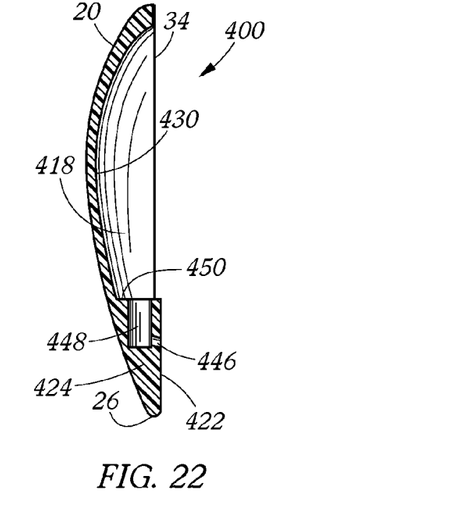
FIG. 22 is a cross sectional view taken along lines 22-22 of FIG. 21.
Figure 23:
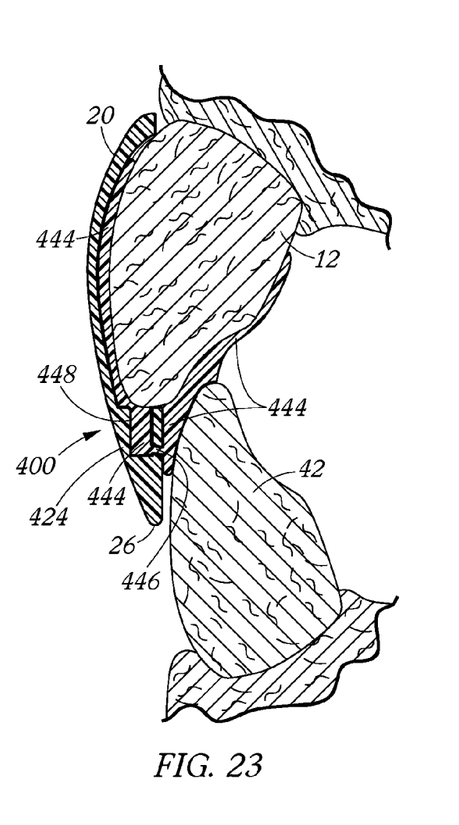
FIG. 23 is a cross sectional view similar to FIG. 22 which additionally shows the tooth cap of FIG. 19 mounted on and attached to a user's real tooth as well as an opposing tooth of the user received in the recessed area of the tooth cap.
Figure 24:
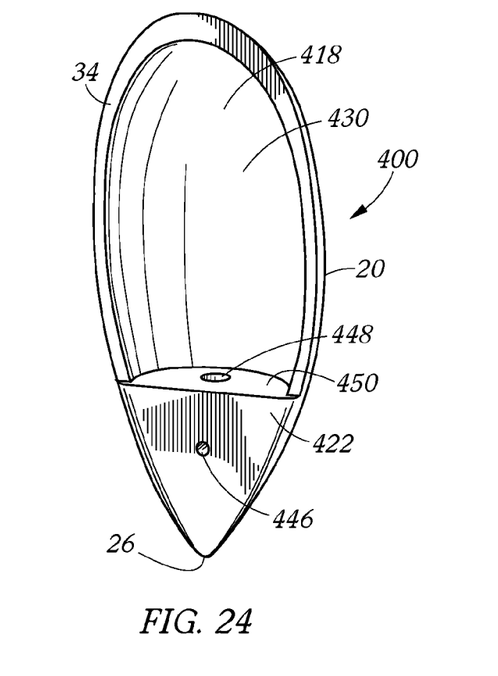
FIG. 24 is a another perspective view of the tooth cap of FIG. 19, showing, however a perspective view of the rear of tooth cap.
Figure 25:
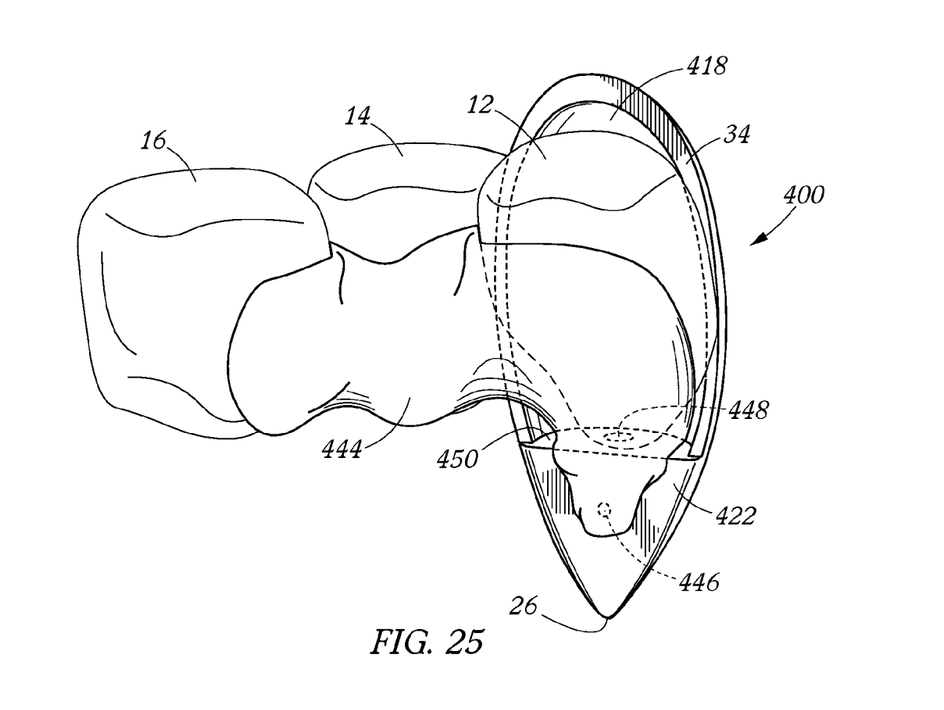
FIG. 25 is a perspective view similar to FIG. 7 showing the tooth cap of FIG. 19 mounted on the left upper canine tooth and anchored to the first and second upper left premolars looking from the inside of a wearer's mouth to the outside. The tooth cap is positioned on the canine tooth and a portion of thermoplastic material extends from the cavity inside the tooth cap to the first and second premolars.

FIGS. 22 and 23 also illustrate that lower extension section 424 which forms tip 26 at the distal end of the tooth cap is solid except for a pair of passageways 446, 448 which are similar to passageways 246, 248 of tooth cap 200 as illustrated in FIGS. 11 and 12. Passageways 446, 448 function in the same manner as passageways 246, 248 in that they receive flowable thermoplastic 444 as shown in FIGS. 23 and 25. As also discussed in connection with tooth cap 200, when the thermoplastic (or other flowable but hardenable attaching material) cools and hardens as shown in FIGS. 23 and 25 about the wearer's tooth 12, in passageways 446, 448 and on the back side 422 of the tooth cap, an extremely strong mechanical bond (anchoring) between the thermoplastic and the tooth cap 400 is provided, thereby insuring that the thermoplastic (or other flowable but hardenable attaching material) will remain securely attached to the tooth cap and as such enable the user to reuse the tooth cap for years if desired.

Figure 26:
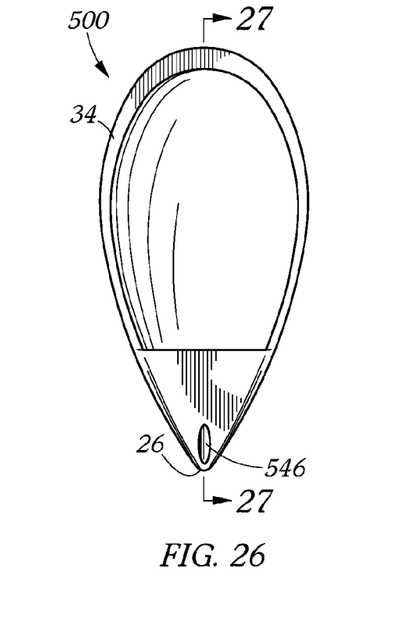
FIG. 26 is a rear elevational view of a tooth cap similar to that of FIG. 19. However, the tooth cap of this embodiment has a different hole than that of the previous embodiment.
Figure 27:
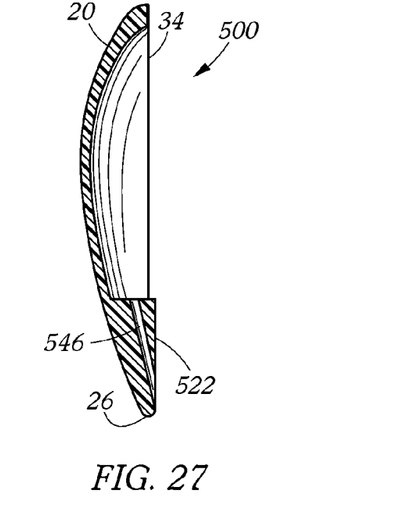
FIG. 27 is a cross sectional view taken along lines 27-27 of FIG. 26.
Figure 28:
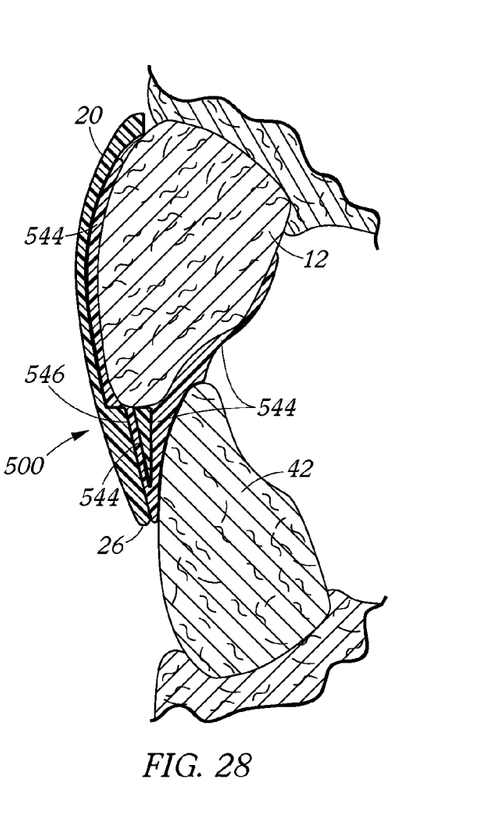
FIG. 28 is a cross sectional view similar to FIG. 27 which additionally shows the tooth cap of FIG. 26 mounted on and attached to a user's real tooth as well as an opposing tooth of the user received in the recessed area of the tooth cap.

FIGS. 26 through 28 illustrate a tooth cap 500 which is very similar to tooth cap 400 except that tooth cap 500 is provided with a single long linear hole 548 instead of passageways 446 and 448. Hole 546 functions in the same manner as passageways 446, 448 in that it receives flowable thermoplastic 544 as shown in FIG. 28. In addition, when the thermoplastic cools and hardens about the wearer's tooth 12, in hole 546 and on the back side 522 of the tooth cap, a strong mechanical bond (anchoring) between the thermoplastic (or other flowable but hardenable attaching material) and the tooth cap 500 will be provided, thereby insuring that the thermoplastic will remain securely attached to the tooth cap and as such enable the user to reuse the tooth cap for years if desired.

While the illustrated embodiments are provided with holes 46, 146, 346 and 546 as well as passageways 246, 248 and 446, 448 for anchoring the thermoplastic or other flowable but hardenable attaching material to the illustrated tooth caps, other surface features such as ridges and depressions could also be employed to enhance attachment of the attaching material to the tooth cap as described in my U.S. Pat. No. 5,547,381.

As indicated, thermoplastic is a preferred material for attaching the tooth cap of the present invention to a real tooth. However, other materials for attaching tooth cap 10 to a real tooth may also be used such as Sea Bond which was used in the application method for attaching the original Fangtastics fang. Other suitable attaching materials include Scarecrow's liner material, Coe-Soft, Scarecrow's newer A & B chemical material, which hardens like an epoxy, Fun World's fang putty, denture adhesive, or any flowable material which later hardens, partially or completely. In fact, the more flowable the attaching material is, the more easily the attaching material will flow into and out through holes provided in the tooth cap such as holes 46, 146, 346 and 546 and/or passageways 246, 248 and 446, 448. Accordingly, any flowable but hardenable material should work as well as thermoplastic. In fact, epoxy like materials may work extremely well since they are generally even more flowable than thermoplastic materials.

While my U.S. Pat. No. 5,547,381 describes a preferred method for attaching the tooth cap of the present invention to a real tooth, a method specifically tailored for applying the tooth cap of the present invention to a real tooth includes the following steps:

1. Providing a tooth cap 10 or similar tooth cap defining a cavity for receiving a real tooth wherein the surface of said cavity is provided with surface features for enhancing the attachment of material for removably attaching said tooth cap to the real tooth;

2. Placing material for removably attaching tooth cap 10 to a real tooth into the cavity of tooth cap 10;

3. Placing tooth cap 10 onto the real tooth so that the attaching material envelops the surface features; and then 4. Biting down to adjust the tooth cap's position on the real tooth so that interference caused by the tooth cap with the user's normal occlusion is minimized; and, 5. While biting down, allowing the attaching material to set so that the tooth cap is affixed to the real tooth in the position which minimizes said interference.

In the embodiments of FIGS. 11-28, the foregoing placing step 3 forces the attaching material down into the holes and passageways of these tooth caps.

The foregoing description is considered as illustrative only of the principles of the invention. Furthermore, since numerous modifications and changes will readily occur to those skilled in the art, it is not desired to limit the invention to the exact construction and process shown and described above. Accordingly, all suitable modifications and equivalents that may be resorted to are considered to be within the scope of the invention as defined by the claims that follow.

What is claimed is:

1. A removable and re-usable tooth cap of the type that is attachable to and removable from a user's real tooth by the user, said tooth cap defining a cavity for receiving a full-size real tooth as well as material for removably attaching said tooth cap to the full-size real tooth, said tooth cap having a front side and a back side which terminate at a distal end of said tooth cap, said cavity including a generally concave surface defined by an inside surface of said front side and wherein said back side has a length which is less than $2/3$ of the overall length of said tooth cap, said back side further defining a hole for receiving said material so that said material anchors or locks to said tooth cap when said material hardens.

2. A tooth cap as claimed in claim 1 wherein the length of said back side is less than $1/2$ of the length of said tooth cap.

3. A tooth cap as claimed in claim 1 wherein the length of said back side is less than $1/3$ of the length of said tooth cap.

4. A tooth cap as claimed in claim 1 wherein the length of said back side is between about $1/5$ and $1/2$ of the length of said tooth cap.

5. A tooth cap as claimed in claim 1 wherein the length of said back side is between about $1/5$ and $1/3$ of the length of said tooth cap.

6. A tooth cap as claimed in claim 1 wherein the length of said back side is between about $1/4$ and $1/3$ of the length of said tooth cap.

7. A tooth cap as claimed in claim 1 wherein said front side and back side converge to a tip at the distal end of the tooth cap so that the tooth cap will look like a fang when attached to a person's real tooth.

8. A tooth cap as claimed in claim 1 wherein said cavity is provided with surface features for enhancing attachment of the attaching material to said tooth cap.

9. A removable and re-usable tooth cap of the type that is attachable to and removable from a user's real tooth by the user, said tooth cap defining a cavity for receiving a real tooth as well as material for removably attaching said tooth cap to the real tooth, said tooth cap having a front side and a back side which terminate at a distal end of said tooth cap, in said cavity including a generally concave surface defined by an inside surface of said front side and wherein said inside surface of said front side terminates at a peripheral edge which adjoins the front surface of said front side, said back side having a length which is less than $1/3$ of the overall length of said tooth cap, said back side also being generally parallel to said peripheral edge, said back side further defining a hole for receiving said material so that said material anchors or locks to said tooth cap when said material hardens.

10. A removable and re-usable tooth cap of the type that is attachable to and removable from a user's real tooth by the user, said tooth cap defining a cavity for receiving a real tooth as well as material for removably attaching said tooth cap to the real tooth, said tooth cap having a front side and a back side which terminate at a distal end of said tooth cap, in said cavity including a generally concave surface defined by an inside surface of said front side and wherein said inside surface of said front side terminates at a peripheral edge which adjoins the front surface of said front side, said front side and back side also defining a lower extension section which forms a tip at the distal end of the tooth cap so that the tooth cap will look like a fang when attached to a person's real tooth, said back side also being generally parallel to said peripheral edge, said lower extension section of said tooth cap further defining a ledge surface which connects said back side to said concave surface of said cavity, said lower extension section also defining a hole in said ledge surface for receiving said material so that said material anchors or locks to said tooth cap when said material hardens.

11. A tooth cap as claimed in claim 10 wherein said cavity is provided with surface features for enhancing attachment of the attaching material to said tooth cap.

12. A tooth cap as claimed in claim 10 wherein said hole extends through said back side.

13. A tooth cap as claimed in claim 10 wherein said hole is defined by a pair of passageways in fluid communication with each other.

14. A tooth cap as claimed in claim 10 wherein said hole makes a bend as it extends from said ledge surface to back side of said tooth cap.

15. A tooth cap as claimed in claim 10 wherein said lower extension section is solid except for said hole.

16. A tooth cap as claimed in claim 10 wherein said ledge surface adjoins said concave surface of said cavity at an angle of about 90 degrees and wherein said ledge surface adjoins said back side at an angle of about 270 degrees.

17. A tooth cap as claimed in claim 1 wherein the length of said back side is less than $1/3$ of the length of said tooth cap.

18. A tooth cap as claimed in claim 1 wherein the length of said back side is about 25 percent of the overall length of said tooth cap.

* * * * *